United States Patent
Kang et al.

(10) Patent No.: US 12,239,663 B2
(45) Date of Patent: Mar. 4, 2025

(54) PHARMACEUTICAL COMPOSITION FOR PREVENTION OR TREATMENT OF LYSOSOMAL STORAGE DISORDERS

(71) Applicants: BIOGRAPHENE INC., Seoul (KR); SEOUL NATIONAL UNIVERSITY R & DB FOUNDATION, Seoul (KR)

(72) Inventors: Kyung-Sun Kang, Seoul (KR); Byung Hee Hong, Suwon-si (KR); Insung Kang, Anyang-si (KR); Je Min Yoo, Seoul (KR); Donghoon Kim, Seoul (KR)

(73) Assignees: BIOGRAPHENE INC., Seoul (KR); SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 844 days.

(21) Appl. No.: 17/310,400

(22) PCT Filed: Jan. 23, 2020

(86) PCT No.: PCT/KR2020/001162
§ 371 (c)(1),
(2) Date: Jul. 30, 2021

(87) PCT Pub. No.: WO2020/159159
PCT Pub. Date: Aug. 6, 2020

(65) Prior Publication Data
US 2022/0096540 A1    Mar. 31, 2022

(30) Foreign Application Priority Data
Jan. 30, 2019    (KR) .................. 10-2019-0011642

(51) Int. Cl.
| | | |
|---|---|---|
| *A61K 33/44* | (2006.01) | |
| *A61K 9/14* | (2006.01) | |
| *A61P 3/06* | (2006.01) | |
| *B82Y 5/00* | (2011.01) | |
| *B82Y 20/00* | (2011.01) | |
| *B82Y 30/00* | (2011.01) | |
| *B82Y 40/00* | (2011.01) | |
| *C01B 32/198* | (2017.01) | |
| *C09K 11/65* | (2006.01) | |

(52) U.S. Cl.
CPC .............. *A61K 33/44* (2013.01); *A61K 9/14* (2013.01); *A61P 3/06* (2018.01); *C01B 32/198* (2017.08); *C09K 11/65* (2013.01); *B82Y 5/00* (2013.01); *B82Y 20/00* (2013.01); *B82Y 30/00* (2013.01); *B82Y 40/00* (2013.01); *C01P 2004/04* (2013.01); *C01P 2004/64* (2013.01); *C01P 2006/60* (2013.01)

(58) Field of Classification Search
None
See application file for complete search history.

(56) References Cited

U.S. PATENT DOCUMENTS

2016/0193249 A1    7/2016    Tour et al.
2017/0189359 A1*   7/2017    Hong .................. A61K 33/44

FOREIGN PATENT DOCUMENTS

| CN | 103845361 A | 6/2014 |
|---|---|---|
| CN | 106470706 A | 3/2017 |
| KR | 10-2013-0122585 A | 11/2013 |
| KR | 10-2015-0115671 A | 10/2015 |
| KR | 10-1747147 B1 | 6/2017 |
| KR | 10-2019-0093416 A | 8/2019 |
| WO | 2020009551 A1 | 1/2020 |

OTHER PUBLICATIONS

Beck, Developmental Medicine and Child Neurology, 60, 2018 (Year: 2018).*
Sheth, The Lancet Regional Health, Southeast Asia, 9, 2023 (Year: 2023).*
Altarescu, Molecular Biology International, 2012 (Year: 2012).*
Hong et al., SB02.03.09 : Therapeutic Applications of Graphene Qmuttum Dots for Central Nervous System Disease. 2019 MRS Fall Meeting & Bahihit. Dec. 2, 2019, Boston, Massachusetts, USA. symposium.
Kim et al., Graphene quantum dots prevent a-sy-nueleinopathy in Pat son's disease. Nature Nanotechnology. Sep. 2018, vol. 13, No. 9, pp. 812-818.
EESR dated Oct. 10, 2022 for the corresponding European Patent Application No. 20749590.4, 11 pages.
Kang et al., Graphene Quantum Dots Alleviate Impaired Functions in Niemann-Pick Disease Type C in Vivo, Nano Letters, 2021, 21, 2339-2346.
Rosenbaum et al., Niemann-Pick type C disease: molecular mechanisms and potential therapeutic approaches, Journal of Neurochemistry, 2011, 116, 789-795.
Chinese Office Action for corresponding Chinese Patent Application No. 202080012042.0, mailed Aug. 1, 2022, six pages, machine translation.

* cited by examiner

*Primary Examiner* — Robert A Wax
*Assistant Examiner* — William Craigo
(74) *Attorney, Agent, or Firm* — Vorys, Sater, Seymour and Pease LLP; Mih Suhn Koh (57) ABSTRACT

Provided is a method for prevention or treatment of a lysosomal storage disorder, and more particularly, to a method that may exhibit excellent efficacy against various lysosomal storage disorders including Niemann-Pick disease by including graphene quantum dots.

4 Claims, 13 Drawing Sheets

PHARMACEUTICAL COMPOSITION FOR PREVENTION OR TREATMENT OF LYSOSOMAL STORAGE DISORDERS

CROSS-REFERENCE TO RELATED APPLICATIONS

This application is a 371 of PCT/KR2020/001162 filed on Jan. 23, 2020, which claims the benefit of priority from Korean Patent Application No. 10-2019-0011642 filed on Jan. 30, 2019, the contents of each of which are incorporated herein by reference in its entirety.

TECHNICAL FIELD

The present invention relates to a pharmaceutical composition for prevention or treatment of a lysosomal storage disorder, and particularly, to a pharmaceutical composition for prevention or treatment of a lysosomal storage disorder, the pharmaceutical composition including graphene quantum dots as an active ingredient.

The present invention claims priority to and the benefit of Korean Patent Application No. 10-2019-0011642, filed on Jan. 30, 2019, the disclosure of which is incorporated herein by reference in its entirety.

BACKGROUND ART

Diseases caused by accumulation of substrates in lysosomes due to abnormal metabolism are lysosomal storage disorders (LSDs). Depending on the symptoms caused by the accumulated substrates, a lysosomal storage disorder appears as, for example, Niemann-Pick disease types A, B, and C, Gaucher disease type II, Fabry disease, gangliosidosis, Tay-Sachs disease, Sandhoff disease, Krabbe disease, and metachromatic leukodystrophy.

For example, Gaucher disease known as the most common lysosomal storage disorder results from accumulation of glucocerebrosides (also known as glycosylceramide) which are glycolipids, and the symptoms include pain, severe neurological complications, swelling of lymph nodes and adjacent joints, abdominal distension, browning of the skin, anemia, low platelet counts, and deposition of yellow fat on the sclera. Also, Niemann-Pick disease is a congenital autosomal recessive lysosomal storage disorder in which sphingomyelin is accumulated in lysosomes in cells, for example, macrophages and neurons, and the symptoms include neurodegeneration, an enlarged liver and spleen, and dyspnea.

The cause of lysosomal storage disorders is still 100% unknown, but the deficiency of a single enzyme required for metabolism of lipids, glycogen, glycoproteins, or mucopolysaccharides is known to be a major factor. For example, Gaucher disease results from the deficiency of glucocerebrosidase, and Niemann-Pick disease results from the deficiency of acidic sphingomyelinase. As described above, because the defective enzymes are different in various diseases known as lysosomal storage disorders, it was not easy to find a treatment generally applicable to the lysosomal storage disorders.

Thus, many studies have been conducted to treat symptoms related to lysosomal storage disorders, but a therapeutic agent that has a common preventive or therapeutic effect on lysosomal storage disorders has not been developed yet.

DISCLOSURE

Technical Problem

The present invention is directed to providing a pharmaceutical composition for prevention or treatment of a lysosomal storage disorder.

However, a technical objective to be achieved by the present invention is not limited to the above-mentioned objective, and other objectives that are not mentioned will be clearly understood by those skilled in the art from the following description.

Technical Solution

One aspect of the present invention provides a pharmaceutical composition for prevention or treatment of a lysosomal storage disorder, the pharmaceutical composition including graphene quantum dots as an active ingredient.

In an embodiment of the present invention, the lysosomal storage disorder may be caused by substrates accumulated in lysosomes.

In another embodiment of the present invention, the graphene quantum dots may inhibit accumulation of substrates in lysosomes or decompose previously accumulated substrates by binding to unmetabolized substrates.

In another embodiment of the present invention, the graphene quantum dots may be nano-sized fragments of graphene oxide or reduced graphene oxide.

In another embodiment of the present invention, the graphene quantum dots may include, as a terminal functional group, an oxygen atom-containing functional group selected from the group consisting of a carboxyl group, a ketone group, an aldehyde group, a hydroxy group, and an epoxy group.

In another embodiment of the present invention, the graphene quantum dots may have a length of 1 nm to 20 nm.

In another embodiment of the present invention, the lysosomal storage disorder may be at least one disease selected from the group consisting of Pompe disease, Gaucher disease, Fabry disease, $G_{M1}$-ganglioside accumulation, Tay-Sachs disease, Sandhoff disease, Niemann-Pick disease, Krabbe disease, Farber disease, metachromatic leukodystrophy, Hurler-Scheie syndrome, Hunter syndrome, Sanfilippo syndrome A, Sanfilippo syndrome B, Sanfilippo syndrome C, Sanfilippo syndrome D, Morquio syndrome A, Morquio syndrome B, Maroteaux-Lamy syndrome, Sly syndrome, alpha-mannosidosis, beta-mannosidosis, Fucosidosis, Sialidosis, and Schindler-Kanzaki disease.

In another embodiment of the present invention, the lysosomal storage disorder may be Niemann-Pick disease.

In another embodiment of the disclosure, the composition may further include a pharmaceutically acceptable carrier or excipient.

Another aspect of the present invention provides a method of preventing or treating a lysosomal storage disorder, the method including administering a pharmaceutical composition including graphene quantum dots as an active ingredient to an individual.

Still another aspect of the present invention provides a use of a pharmaceutical composition for preventing or treating a lysosomal storage disorder, the pharmaceutical composition including graphene quantum dots as an active ingredient.

Yet another aspect of the present invention provides a use of graphene quantum dots for preparing a medicine used for prevention or treatment of a lysosomal storage disorder.

Advantageous Effects

A pharmaceutical composition according to the present invention includes graphene quantum dots and exhibits an effect of inhibiting accumulation of substrates in lysosomes or decomposing previously accumulated substrates by binding to unmetabolized substrates using a negative charge generated on a surface of the graphene quantum dot, and thus, can prevent or treat a lysosomal storage disorder.

MODES OF THE INVENTION

A pharmaceutical composition for prevention or treatment of a lysosomal storage disorder of the present invention includes graphene quantum dots as an active ingredient.

Throughout the present specification, the term "graphene" means that a plurality of carbon atoms are linked to each other via a covalent bond to form a polycyclic aromatic molecule, and the carbon atoms linked via the covalent bond form a 6-membered ring as a basic repeating unit, but may further include a 5-membered ring and/or a 7-membered ring.

Throughout the present specification, the term "graphene quantum dots (GQDs)" refers to nano-sized fragments of graphene oxide or reduced graphene oxide.

Throughout the present specification, the term "graphene oxide" is also referred to as "graphene oxides" and may be abbreviated to "GOs". In detail, the graphene oxide may include a structure in which a functional group containing an oxygen atom such as a carboxyl group, a hydroxy group, or an epoxy group is bonded onto graphene, but is not limited thereto.

Throughout the present specification, the term "reduced graphene oxide" refers to graphene oxide having a reduced oxygen atom ratio through a reduction process, and may be abbreviated to "rGQDs".

Throughout the present specification, the term "nano-graphene oxides" refers to nanoscale graphene oxides having an average diameter of 15 nm or more and an average height of 5 nm or more, and may be abbreviated to "nano-GOs".

Graphene quantum dots according to the present invention each have a surface exhibiting a negative charge. In detail, the graphene quantum dots according to the present invention may include, as a terminal functional group, an oxygen atom-containing functional group selected from the group consisting of a carboxyl group, a ketone group, an aldehyde group, a hydroxy group, and an epoxy group. Specifically, the graphene quantum dots may include, as a main functional group, the carboxyl group exhibiting a negative charge.

In the present invention, graphene quantum dots may inhibit accumulation of substrates in lysosomes or decompose previously accumulated substrates by binding to unmetabolized substrates using a negative charge generated on a quantum dot surface. In detail, the graphene quantum dots change characteristics of insoluble substrates to water-soluble by binding to unmetabolized substrates accumulated in the form of insoluble substrates using a negative charge generated on a quantum dot surface, and the graphene quantum dots not only inhibit accumulation of substrates in lysosomes by exiting the lysosomes while the substrates are bound thereto, but also induce decomposition of previously accumulated substrates.

In the present invention, a lysosomal storage disorder (LSD) refers to a disease caused by accumulation of substrates such as lipids, glycogen, glycoproteins, or mucopolysaccharides in lysosomes due to abnormal metabolism. In detail, the lysosomal storage disorder may be at least one disease selected from the group consisting of Pompe disease, Gaucher disease, Fabry disease, $G_{M1}$-ganglioside accumulation, Tay-Sachs disease, Sandhoff disease, Niemann-Pick disease, Krabbe disease, Farber disease, metachromatic leukodystrophy, Hurler-Scheie syndrome, Hunter syndrome, Sanfilippo syndrome A, Sanfilippo syndrome B, Sanfilippo syndrome C, Sanfilippo syndrome D, Morquio syndrome A, Morquio syndrome B, Maroteaux-Lamy syndrome, Sly syndrome, alpha-mannosidosis, beta-mannosidosis, Fucosidosis, Sialidosis, and Schindler-Kanzaki disease, but is not limited thereto.

There may be several causes of accumulation of substrates in lysosomes. Mostly, the LSD may be a disease that results from defects in lysosomal function, specifically, accumulation of substrates in a lysosome of a cell due to deficiency of a single enzyme required for metabolism of lipids, glycogen, glycoproteins, or mucopolysaccharides. Alternatively, the LSD may be a disease caused by accumulation of substrates in lysosomes due to disruption of a material transport system due to an abnormality in a gene related to an intracellular material transport system.

The present inventors have made intensive research efforts to develop a therapeutic agent capable of treating symptoms related to lysosomal storage regardless of the cause of the substrate accumulation, and thus, have confirmed that the LSD may be prevented or treated by using graphene quantum dots to decompose unmetabolized substrates. The present invention is based on this.

In a preferred embodiment of the present invention, the lysosomal storage disorder may be Niemann-Pick disease.

The Niemann-Pick disease is a congenital autosomal recessive lysosomal storage disorder characterized by excessive accumulation of sphingomyelin in lysosomes of cells, for example, macrophages and neurons, and impairs normal cell function. Niemann-Pick disease type A results from deficiency of acidic sphingomyelinase and is a rapidly progressive neurodegenerative disease and a disease that typically leads to death at the age of 2 to 3. Niemann-Pick disease type B results in an enlarged liver and spleen and dyspnea, and is generally a milder form leading to death in early adulthood. Both of the two types of Niemann-Pick disease are associated with deficiency of acidic sphingomyelinase (ASM), and are collectively referred to as Niemann-Pick disease or ASM deficiency (ASMD). Another type of the Niemann-Pick disease, for example, type C, does not involve mutations in ASM genes and is not directly responsible for functions of ASM, and results from mutations in NPC1 and NPC2 genes. In Niemann-Pick disease type C, a protein product of a major mutated gene NPC1 is not an enzyme and functions as a transporter in an endosomal-lysosomal system, which moves large water-insoluble molecules through a cell. Also, a protein encoded by the NPC2 gene is a small cholesterol-binding protein present in a lysosomal lumen. Thus, mutations in the NPC1 and NPC2 genes disrupt a transport system of intracellular materials, leading to accumulation of cholesterol and glycolipids in lysosomes.

The graphene quantum dots of the present invention have a nanoscale size, and thus may easily pass through the blood-brain barrier (BBB).

To this end, the graphene quantum dots of the present invention may have an average length of about 1 nm to about 20 nm. Preferably, the average length may be 1 nm to 10 nm, more preferably, 1 nm to 5 nm, most preferably, 1.5 nm to 4 nm, but is not limited thereto. Also, a height may be preferably 0.5 nm to 5 nm, more preferably, 0.5 nm to 3 nm, most preferably, 1.5 nm to 2.5 nm, but is not limited thereto.

Figure 7:
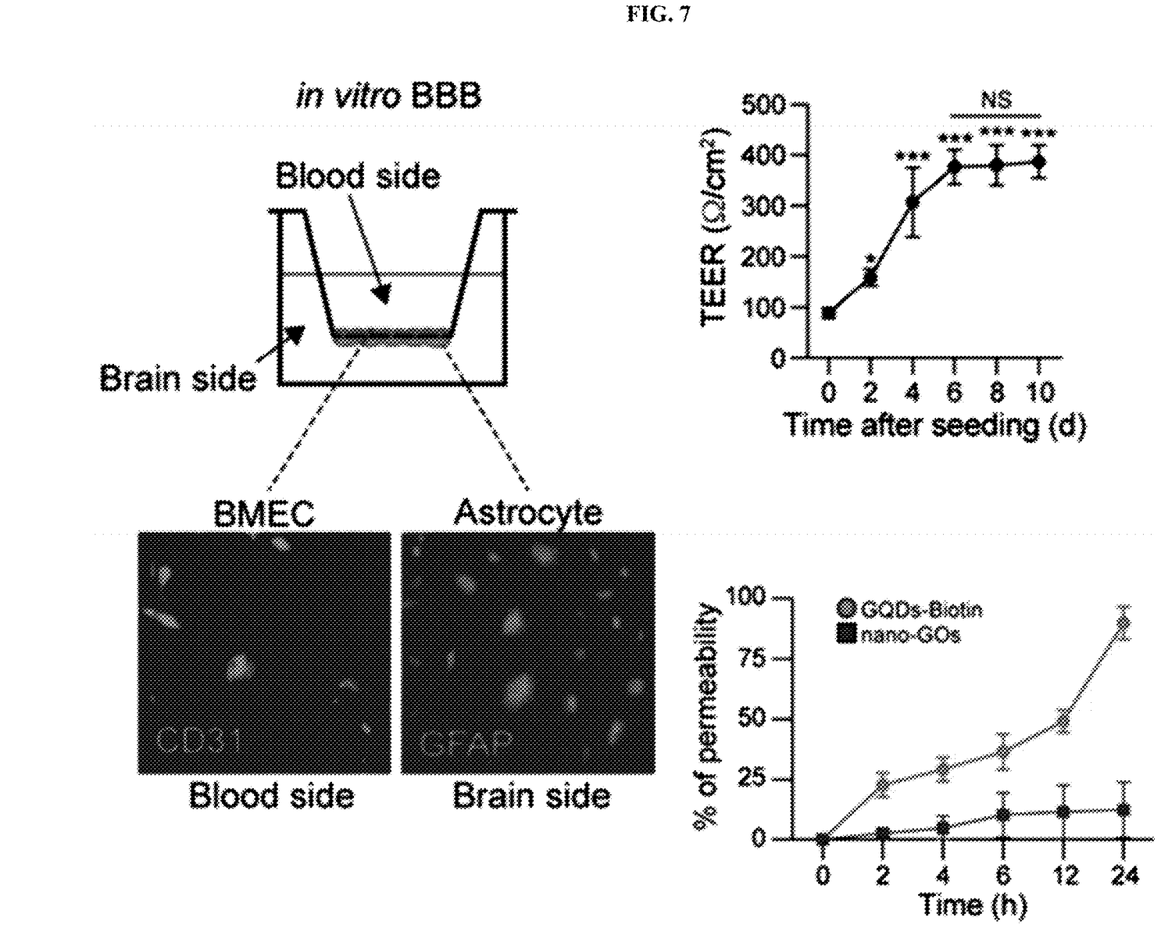
FIG. 7 is a result of blood-brain barrier (BBB) permeation of graphene quantum dots.
Figure 9:
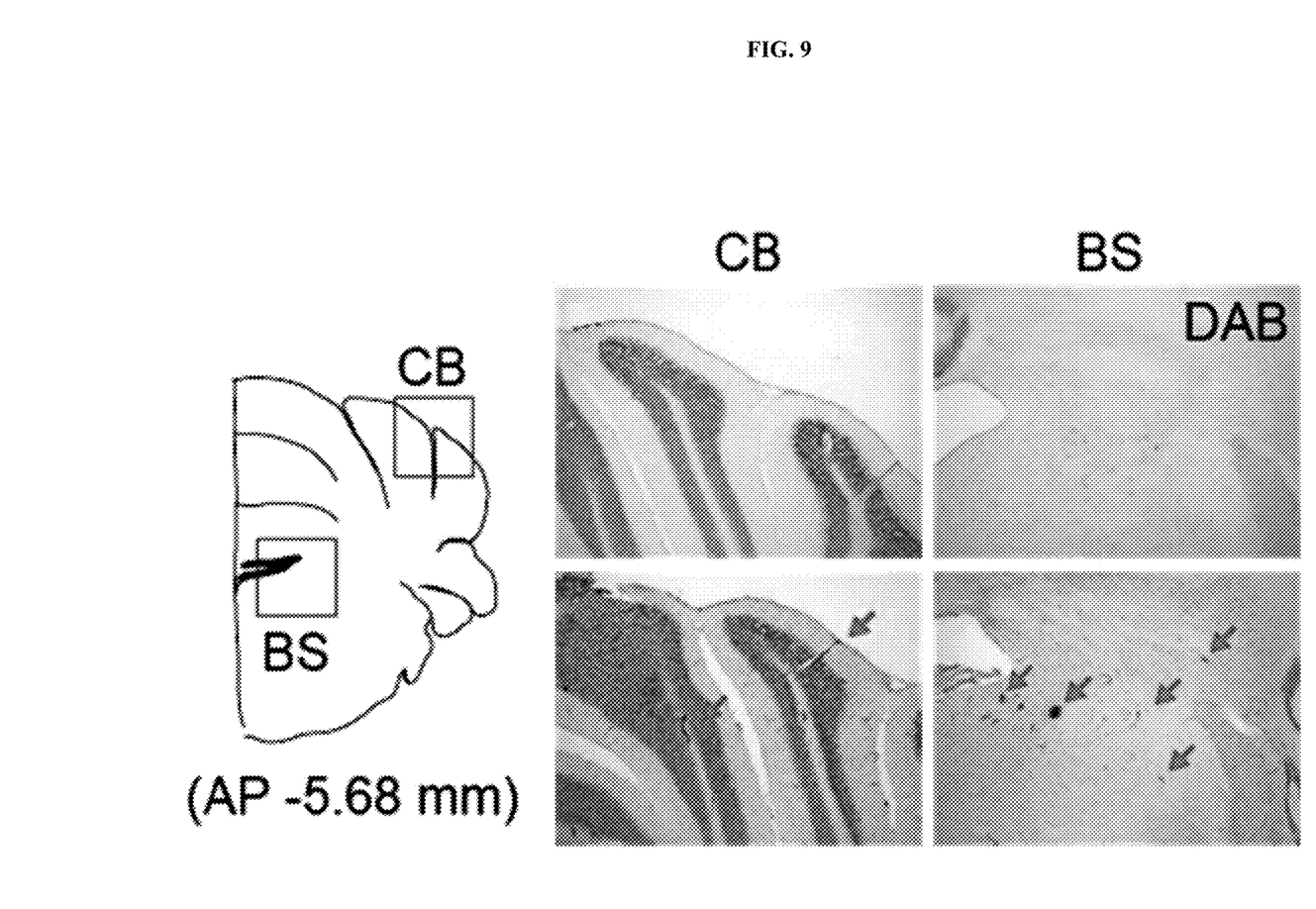
FIG. 9 is a result of BBB permeation of graphene quantum dots.

In an experiment in which GQDs according to an embodiment of the present invention passed through the BBB, when permeability of GOs and GQDs was measured, it was confirmed that the permeability of the GQDs was remarkably increased (FIG. 7). Also, in an experiment of in vitro BBB permeability of graphene quantum dots, when GQD-biotin was injected into the abdomen of rats and then the cerebellum of the rats on which the experiment was focused was treated with a biotin-antibody, GQDs were detected in the cerebellum of the rats treated with the GQD-biotin (FIG. 9).

Furthermore, the graphene quantum dots of the present invention were found not to accumulate in the body.

Thus, the graphene quantum dots according to the present invention may be usefully utilized as a therapeutic agent for lysosomal storage disorders.

Figure 1:
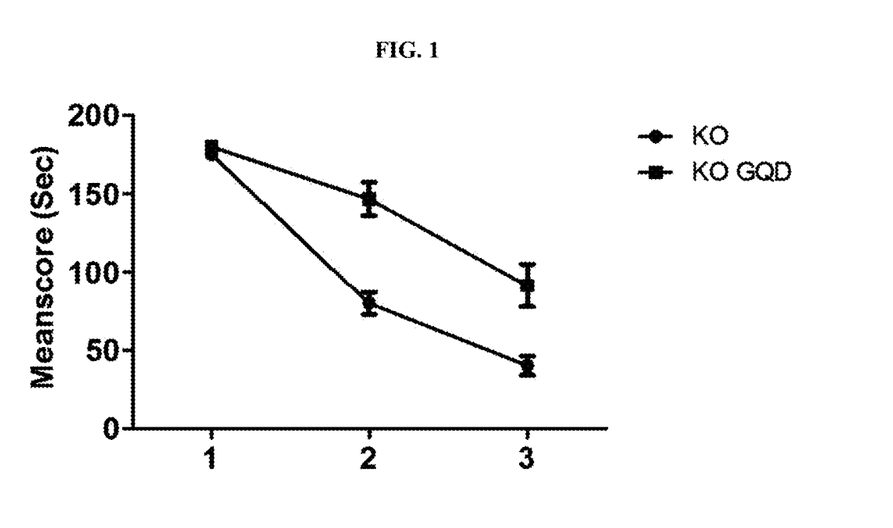
FIG. 1 is a result of analysis of motility of Niemann-Pick disease-induced models by application of graphene quantum dots.
Figure 2:
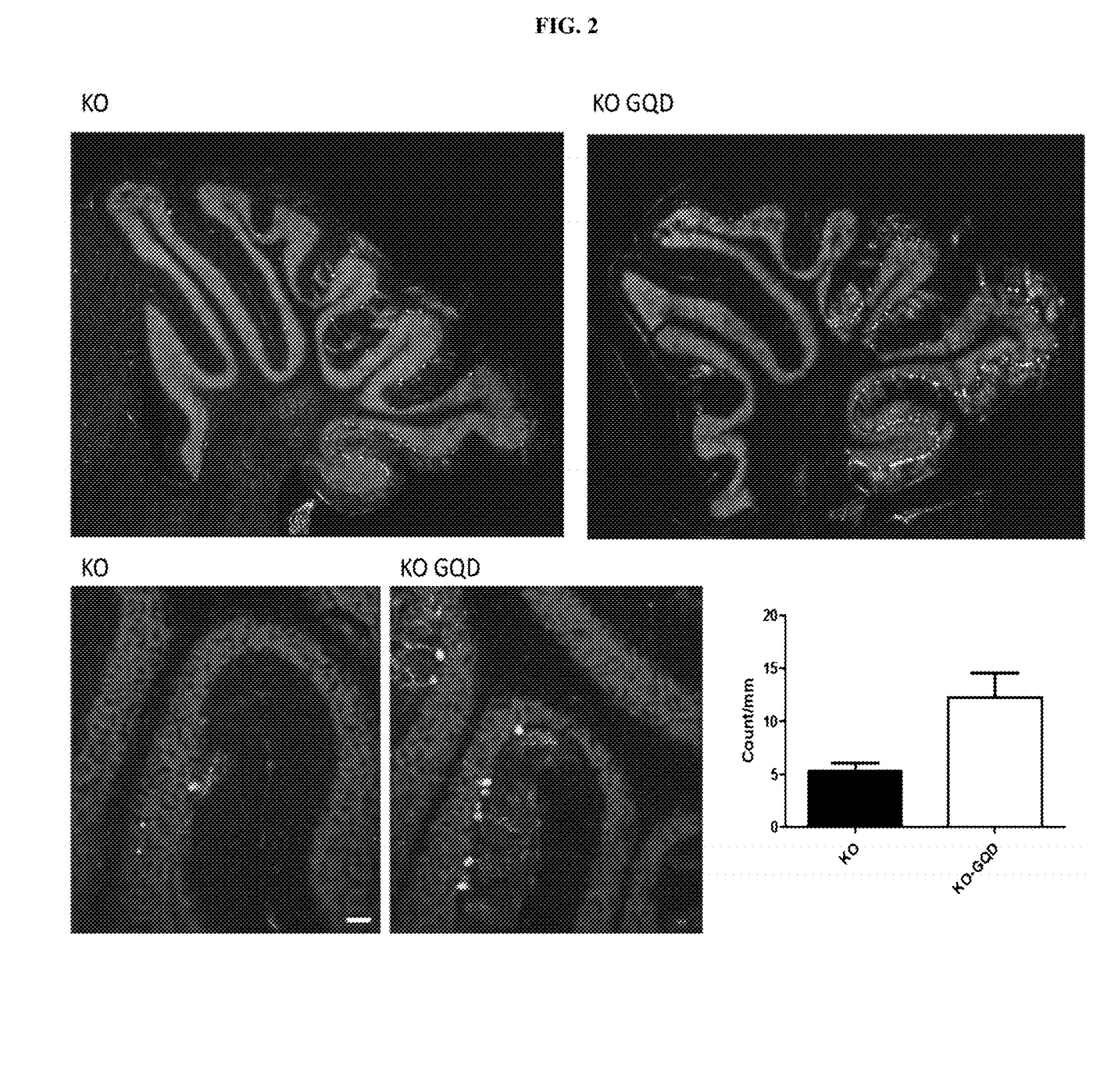
FIG. 2 is a result of analysis of survival of Purkinje cells in the cerebellum of Niemann-Pick disease-induced models by application of graphene quantum dots.
Figure 3:
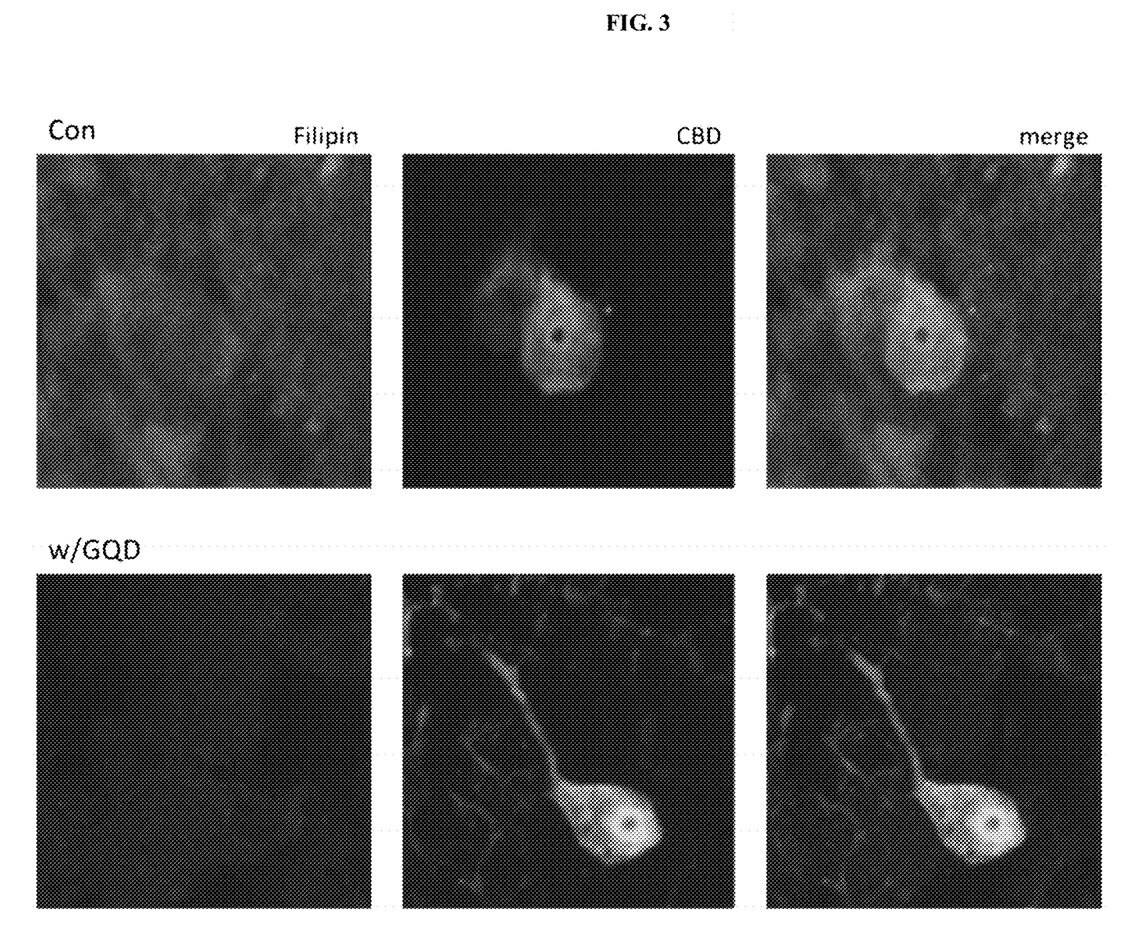
FIG. 3 is a result of reducing cholesterol deposition in Purkinje cells by application of graphene quantum dots.
Figure 4:
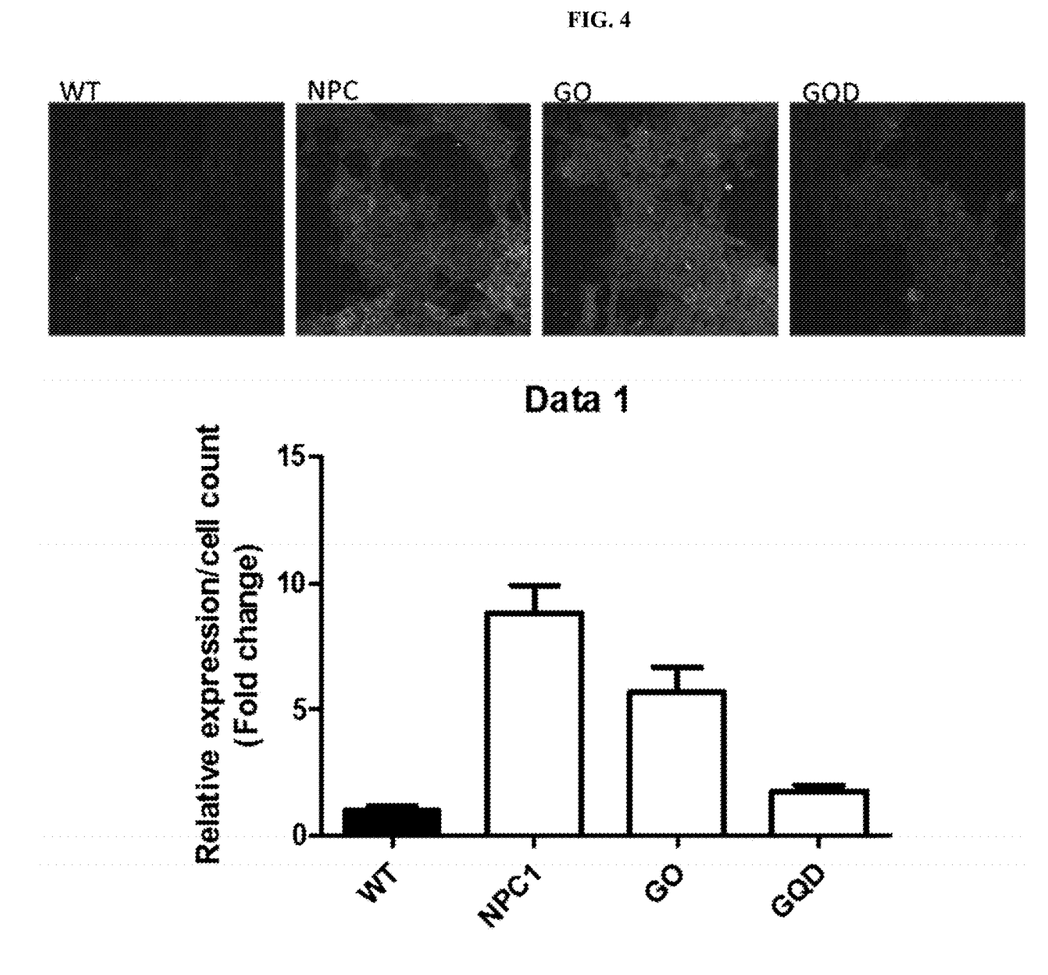
FIG. 4 is a result of reducing cholesterol deposition in human-derived cells by application of graphene quantum dots.
Figure 5:
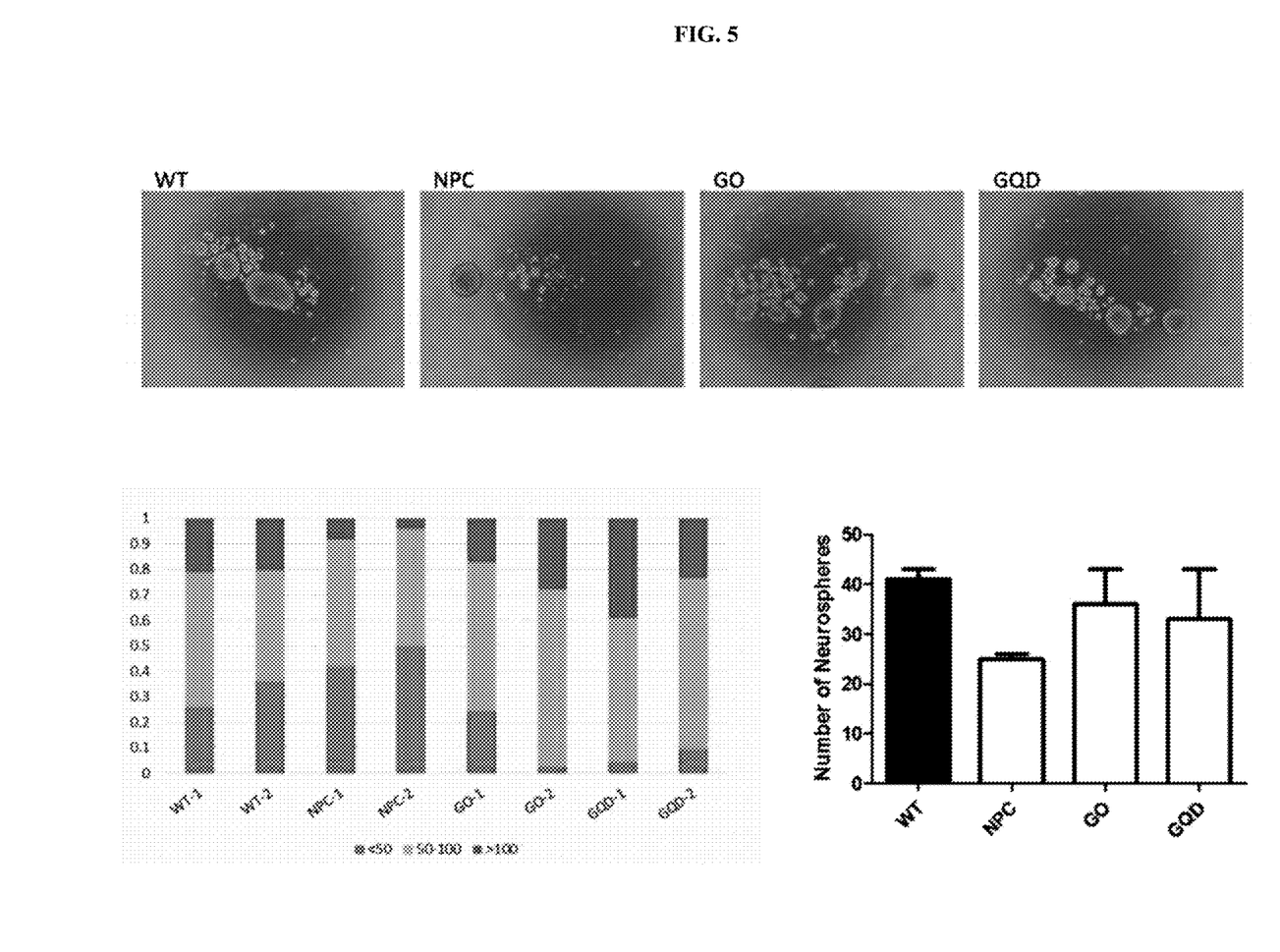
FIG. 5 is a result of improvement in division potency in human-derived cells by application of graphene quantum dots.
Figure 6:
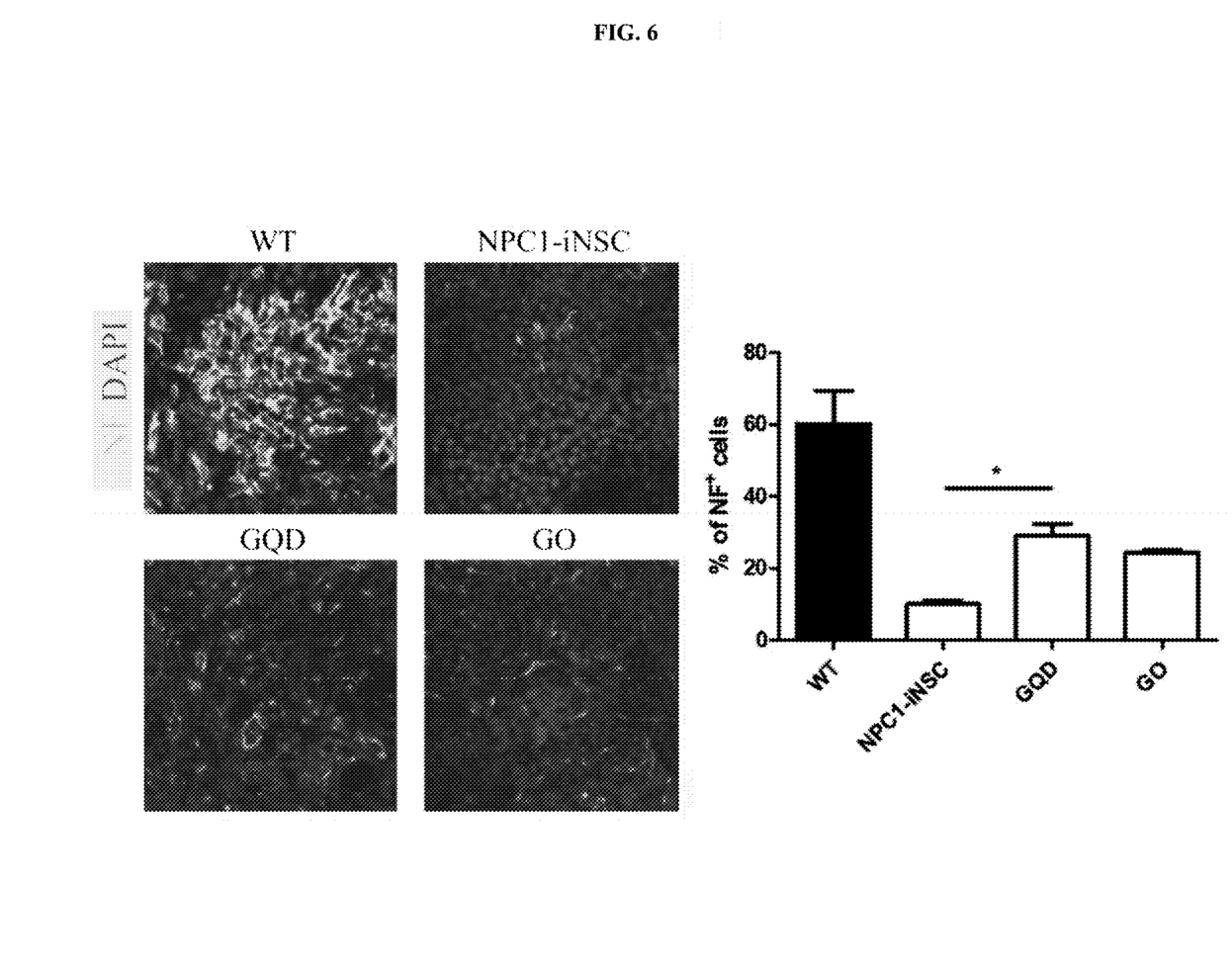
FIG. 6 is a result of improvement in differentiation potency in human-derived cells by application of graphene quantum dots.

According to an embodiment of the present invention, in an experiment that analyzed motility of Niemann-Pick disease-induced models by application of graphene quantum dots, when GQDs were intraperitoneally injected into Niemann-Pick disease-induced rats and motility was measured, recovery of motility was observed in a group in which GQDs were intraperitoneally injected (FIG. 1). Also, as a result of a survival analysis experiment on Purkinje cells in the cerebellum of the Niemann-Pick disease-induced models by application of graphene quantum dots, it was found that the survival of Purkinje cells was increased in the group administered GQDs (FIG. 2). Also, as a result of analyzing the effect of reducing cholesterol deposition in Purkinje cells, it was observed that cholesterol was deposited in Purkinje cells (con) of Niemann-Pick disease-induced rats, whereas deposition symptoms were relieved in the GQD-administered group (FIG. 3). In addition, in an experiment that verified usability in human bodies using induced nerve stem cells (iNSCs), as a result of testing the effects of GQDs on neurons after producing iNSCs using fibroblasts derived from Nieman-Pick patients, a phenomenon in which cholesterol was deposited in the patient-derived iNSCs was observed, and it was observed that an excellent effect compared to GOs which is the same graphene-derived material was shown (FIG. 4). Also, in an experiment where division potency was measured in human-derived cells, it was confirmed that the division of cells was significantly decreased in iNSCs derived from Niemann-Pick patients, and it was observed that division potency was recovered when GQDs were applied (FIG. 5), and it was confirmed that the differentiation into neuronal cells was significantly decreased in iNSCs derived from Niemann-Pick patients, and it was observed that differentiation potency was recovered and significantly improved compared to GOs when GQDs were applied (FIG. 6).

In the present invention, the term "pharmaceutical composition" refers to a composition administered for a specific purpose. For the purposes of the present invention, the pharmaceutical composition of the present invention includes graphene quantum dots and treats or prevents lysosomal storage disorders, and may be formulated by including a compound involved therein and a pharmaceutically acceptable carrier, diluent, or excipient. The pharmaceutical composition according to the present invention includes an active ingredient of the present invention in an amount of 0.1 wt % to 50 wt % based on a total weight of the composition.

Examples of the carrier, excipient, and diluent may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oils.

The pharmaceutical composition of the present invention may be formulated as an oral dosage form such as a discutient, granule, tablet, capsule, suspension, emulsion, syrup, and aerosol, an external preparation, a suppository, or a sterile injectable solution form according to conventional methods in order to be prepared as a pharmaceutical formulation, and generally, may be prepared using diluents or excipients such as fillers, extenders, binders, wetting agents, disintegrating agents, and surfactants, which are usually used in formulation.

Examples of solid formulations for oral administration include tablets, pills, discutients, granules, and capsules, and such solid formulations may be prepared by mixing the pharmaceutical composition with at least one excipient such as starch, calcium carbonate, sucrose, lactose, and gelatin. Also, in addition to simple excipients, lubricants such as magnesium stearate and talc may also be used. Examples of liquid formulations for oral use may include suspensions, liquid solutions, emulsions, and syrups, and in addition to water and liquid paraffin, which are commonly used simple diluents, various excipients such as wetting agents, sweetening agents, fragrances, and preservatives may be included.

Formulations for parenteral administration include sterilized aqueous solutions, non-aqueous solutions, suspensions, emulsions, lyophilized formulations, and suppositories. As the non-aqueous solutions and the suspensions, propylene glycol, polyethylene glycol, vegetable oils such as olive oil, and injectable esters such as ethyl oleate may be used. As a base for the suppositories, Witepsol, Macrogol, Tween 61, cacao butter, laurin butter, glycerogelatin, and the like may be used.

The pharmaceutical composition of the present invention may be administered orally or parenterally (for example, intravenously, subcutaneously, intraperitoneally, or topically) according to a desired method, and specifically, may be administered parenterally, and a dosage range varies according to a patient's age, sex, weight, health status, diet, administration time, administration method, excretion rate, and disease severity. A daily dosage of the pharmaceutical composition according to the present invention is about 0.1 mg/kg to 100 mg/kg, preferably, 1 mg/kg to 30 mg/kg, and may be administered once or several times a day.

The pharmaceutical composition of the present invention may further include at least one active ingredient exhibiting the same or similar medicinal effects in addition to the graphene quantum dots according to the present invention.

In the present invention, the term "prevention" refers to any action of inhibiting lysosomal storage disorders or delaying the onset of lysosomal storage disorders by administration of graphene quantum dots according to the present invention.

In the present invention, the term "treatment" refers to any action in which symptoms of a lysosomal storage disorder are improved or beneficially changed by administration of graphene quantum dots according to the present invention.

In the present invention, the term "inhibition" means preventing the onset of lysosomal storage disorders, reducing symptoms, or treating lysosomal storage disorders by administration of graphene quantum dots according to the present invention.

One aspect of the present invention, the present invention provides a health functional food composition for preventing or improving a lysosomal storage disorder, the health functional food composition including graphene quantum dots as an active ingredient.

The term "improvement" used in the present invention refers to any action that at least reduces parameters related to the condition being treated, for example, symptoms.

The health functional food composition according to the present invention may add the active ingredient to food as it is or may be used with other food or food ingredients, and may be appropriately used according to a conventional method. A mixing amount of the active ingredient may be appropriately determined depending on the purpose of use (for prevention or improvement). The health functional food composition includes at least one of a carrier, a diluent, an excipient, and an additive, and is formulated as one selected from the group consisting of tablets, pills, discutients, granules, powders, capsules, and liquid formulations.

Examples of food that may be added to the composition of the present invention include various foods, powders, granules, tablets, capsules, syrups, beverages, gums, teas, vitamin complexes, and health functional foods. As an additive that may be further included in the present invention, at least one component selected from the group consisting of a natural carbohydrate, a flavoring agent, a nutrient, a vitamin, a mineral (electrolyte), a sweetener (synthetic sweetener, natural sweetener, etc.), a coloring agent, a filling agent, pectic acid and a salt thereof, alginic acid and a salt thereof, an organic acid, a protective colloidal thickener, a pH adjusting agent, a stabilizing agent, a preservative, an antioxidant, glycerin, an alcohol, a carbonation agent, and pulp may be used. Examples of the natural carbohydrates include general sugars, such as monosaccharides such as glucose and fructose; disaccharides such as maltose and sucrose; and polysaccharides such as dextrin and cyclodextrin, and sugar alcohols such as xylitol, sorbitol, and erythritol. As the sweetener, a natural sweetener (thaumatin, stevia extracts (for example, rebaudioside A, glycyrrhizin, etc.)) and a synthetic sweetener (saccharin, aspartame, etc.) may be advantageously used.

In addition, the composition according to the present invention may contain various nutrients, vitamins, minerals (electrolytes), flavoring agents such as synthetic flavoring agents and natural flavoring agents, coloring agents, filling agents, pectic acid and salts thereof, alginic acid and salts thereof, organic acids, protective colloidal thickeners, pH adjusting agents, stabilizing agents, preservatives, glycerin, alcohols, carbonation agents used in carbonated beverages, or the like.

Also, the present invention provides a method of preventing or treating a lysosomal storage disorder, the method including administering a pharmaceutical composition including graphene quantum dots as an active ingredient to an individual.

Also, the present invention provides a use of a pharmaceutical composition for preventing or treating a lysosomal storage disorder, the pharmaceutical composition including graphene quantum dots as an active ingredient.

Also, the present invention provides a use of graphene quantum dots for preparing a medicine used for prevention or treatment of a lysosomal storage disorder.

In the present invention, the term "individual" refers to a subject to which the graphene quantum dots of the present invention may be administered, and the pharmaceutical composition of the present invention may be administered to subjects including mammals such as rats, mice, dogs, cats, horse, cows, and humans by various routes, but is not limited thereto.

In the present invention, the term "administration" means providing a predetermined composition of the present invention to an individual by any appropriate method.

Hereinafter, the present invention will be described in more detail by the following Examples and Experimental Examples. However, the following Examples and Experimental Examples are for illustrative purposes only, and the scope of the present invention is not limited thereto.

EXAMPLE 1

Manufacture of Graphene Quantum Dot (GQD)

Figure 10:
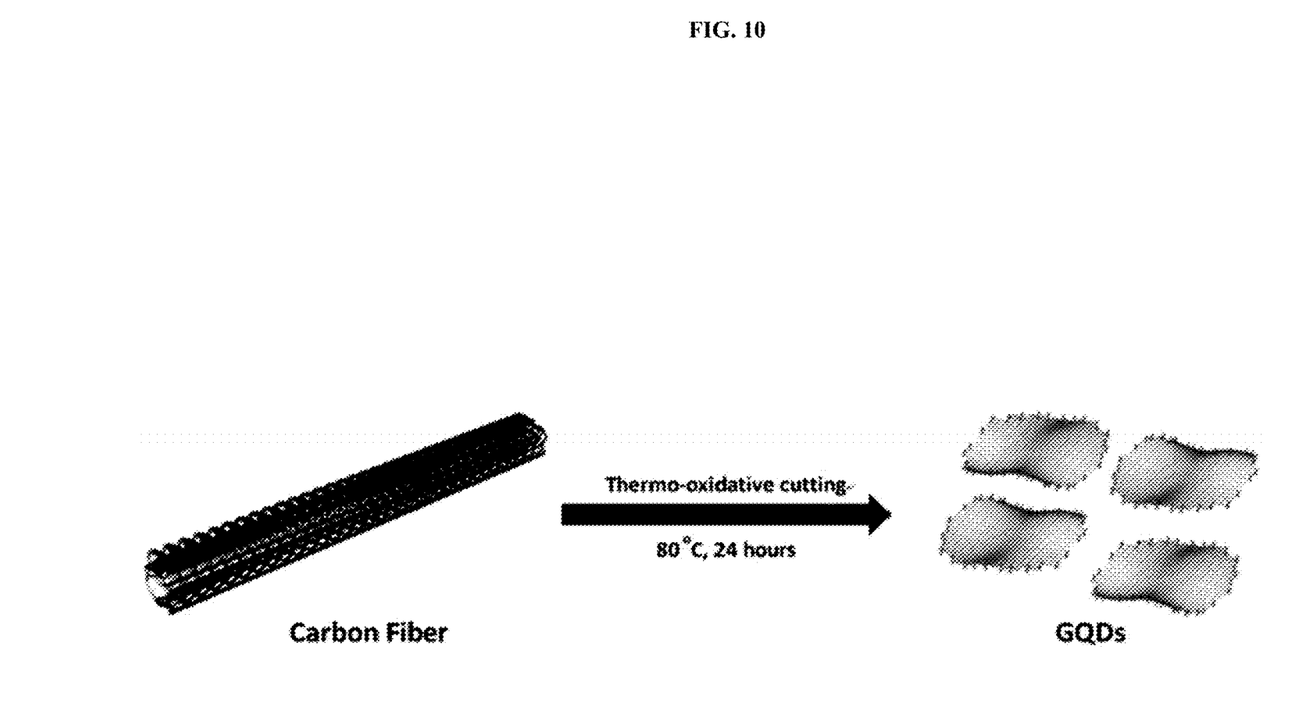
FIG. 10 is a schematic view of a reaction for preparing graphene quantum dots.

GQDs were produced using thermo-oxidative cutting technique using carbon fiber as a raw material (FIG. 10).

In detail, carbon fiber was added to a solution, in which sulfuric acid and nitric acid were mixed at a ratio of 3:1, and then heated at 80° C. for 24 hours (thermo-oxidation process). After the reaction was completed, it was purified through dialysis process, vacuum filtration, etc., and finally GQDs in powder form were obtained with Rotovap. The GQDs thus produced were obtained in the form of nano-sized particles with various structural sizes (from about 1 nm to about 20 nm).

EXPERIMENTAL EXAMPLE 1

Analysis of Motility of Niemann-Pick Disease-Induced Models by Application of Graphene Quantum Dots In order to analyze the therapeutic effect of graphene quantum dots on a lysosomal storage disorder, 300 μg of the GQDs prepared in Example 1 was intraperitoneally injected into Niemann-Pick disease-induced rats once a week for 2 weeks to 8 weeks. In the case of the Niemann-Pick disease-induced rats, in order to mimic a mutation of an NPC1 protein, which is the most important factor in Niemann-Pick disease, NPC1 gene knockout was performed on the rats to cause the disease, and the rats were purchased from Jackson Laboratories.

For 4 weeks or 5 weeks, the motility of the rats was preliminarily measured, only individuals which walked forward on a Rotarod for 180 seconds were selected and used in this experiment, and the result is shown in FIG. 1.

As shown in FIG. 1, when motility was measured at week 6 (1), week 7 (2), and week 8 (3), recovery of motility was observed in the group in which GQDs were injected into the abdominal cavity.

EXPERIMENTAL EXAMPLE 2

Analysis of Survival of Purkinje Cells in Cerebellum of Niemann-Pick Disease-Induced Models by Application of Graphene Quantum Dots The cerebellum of the Niemann-Pick disease-induced models was stained using immunocytochemistry (ICC), wherein the cerebellum includes calbindin which is a protein specifically expressed in Purkinje cells, and the Purkinje cells can be stained using an antibody of the protein.

The Purkinje cells stained using ICC were observed using an immunostaining method of labeling an antibody that recognizes a calbindin protein specifically expressed in Purkinje cells, the number of the cells was quantified using ImageJ software (version. 1.46r, US National Institutes of Health, Bethesda, MD, USA), and the result is shown in FIG. 2.

As shown in FIG. 2, it was observed that survival of the Purkinje cells was increased in the group administered GQDs.

EXPERIMENTAL EXAMPLE 3

Analysis of Effects of Reducing Cholesterol Deposition in Purkinje Cells

Filipin was used to stain cholesterol in order to identify the degree to which cholesterol is deposited in Purkinje cells, and cholesterol deposition in the cytoplasm of the Purkinje cells was observed via ICC co-staining using a calbindin antibody. In detail, the cells were fixed in a 4% paraformaldehyde (PFA) PBS solution for 15 minutes at room temperature, treated with 0.25% Triton X-100 (Sigma) for 10 minutes, and incubated with filipin for 1 hour at room temperature, and then DAPI (Sigma) staining was performed for 5 minutes to stain nuclei. Deposition of the filipin was observed by fluorescence expression using a confocal microscope (Eclipse TE200, Nikon, Japan), the expression level was quantified using ImageJ software (version 1.46r, US National institutes of Health, Bethesda, MD, USA), and the results are shown in FIG. 3.

As shown in FIG. 3, it was confirmed that cholesterol was deposited in the Purkinje cells (con) of the Niemann-Pick disease-induced rats, whereas deposition symptoms were alleviated in the GQD-administered group.

EXPERIMENTAL EXAMPLE 4

Verification of Usability in Human Bodies Using Induced Nerve Stem Cells (iNSCs)

4-1. Analysis of Cholesterol Deposition in Human-Derived Cells

Niemann-Pick patient-derived fibroblasts (fibroblast-GM03123) purchased from the Coriell Institute were used to produce induced neural stem cells (iNSCs), and then the effect of GQDs on neurons was tested.

Specifically, in the same manner as in Experimental Example 3, deposition of cholesterol was observed via filipin staining, fluorescence expression was observed using a confocal microscope (Eclipse TE200, Nikon, Japan), the expression level was quantified using ImageJ software (version 1.46r, US National Institutes of Health, Bethesda, MD, USA), and the result is shown in FIG. 4.

As shown in FIG. 4, it was confirmed that a phenomenon in which cholesterol was deposited in the Niemann-Pick patient-derived iNSCs was observed, whereas the group treated with GQDs showed an excellent effect compared to the group treated with graphene oxide (GO) which is the same graphene-derived material.

4-2. Measurement of Division Potency in Human-Derived Cells (1) It was confirmed that the division of cells was significantly decreased in the Niemann-Pick patient-derived iNSCs, and it was observed that division potency was recovered when GQDs were applied (FIG. 5). Division potency is not expressed in neural stem cells, but may be defined as the degree of expression of neurofilament expressed in differentiated neurons. The cells were fixed in a 4% paraformaldehyde (PFA) PBS solution for 15 minutes at room temperature and then treated with 0.25% Triton X-100 (Sigma) for 10 minutes to increase permeability (cells were permeabilized). The fixed cells were incubated with a blocking solution (5% normal goat serum) for 1 hour at room temperature and incubated with a primary antibody overnight at 4° C. Afterwards, the cells were incubated with a secondary antibody labeled with Alexa Fluor 594 (Invitrogen), and DAPI (Sigma) staining was performed for 5 minutes to stain a nucleus. Images were collected using a confocal microscope (Eclipse TE200, Nikon, Japan). The expression level was quantified using ImageJ software (version 1.46r, US National lnstitutes of Health, Bethesda, MD, USA).

(2) It was confirmed that differentiation into a neuronal cell was significantly decreased in the Niemann-Pick patient-derived iNSCs, and it was observed that differentiation potency was recovered when GQDs were applied. Likewise, it was confirmed that GQD application showed significantly improved differentiation potency compared to GO (FIG. 6).

EXPERIMENTAL EXAMPLE 5

Blood-Brain Barrier (BBB) Permeation of GQD 5-1. In Vitro BBB Assay

Brain microvascular endothelial cells (BMECs) and astrocytes were used to prepare an in vitro BBB assay using a transwell system, and transepithelial electrical resistance (TEER) was measured to show that this assay mimics the BBB. In this experiment, when the permeability of GOs and GQDs was measured, it was confirmed that permeability of the GQDs was significantly increased (FIG. 7).

5-2. In Vivo BBB Permeability of Graphene Quantum Dot

Figure 8:
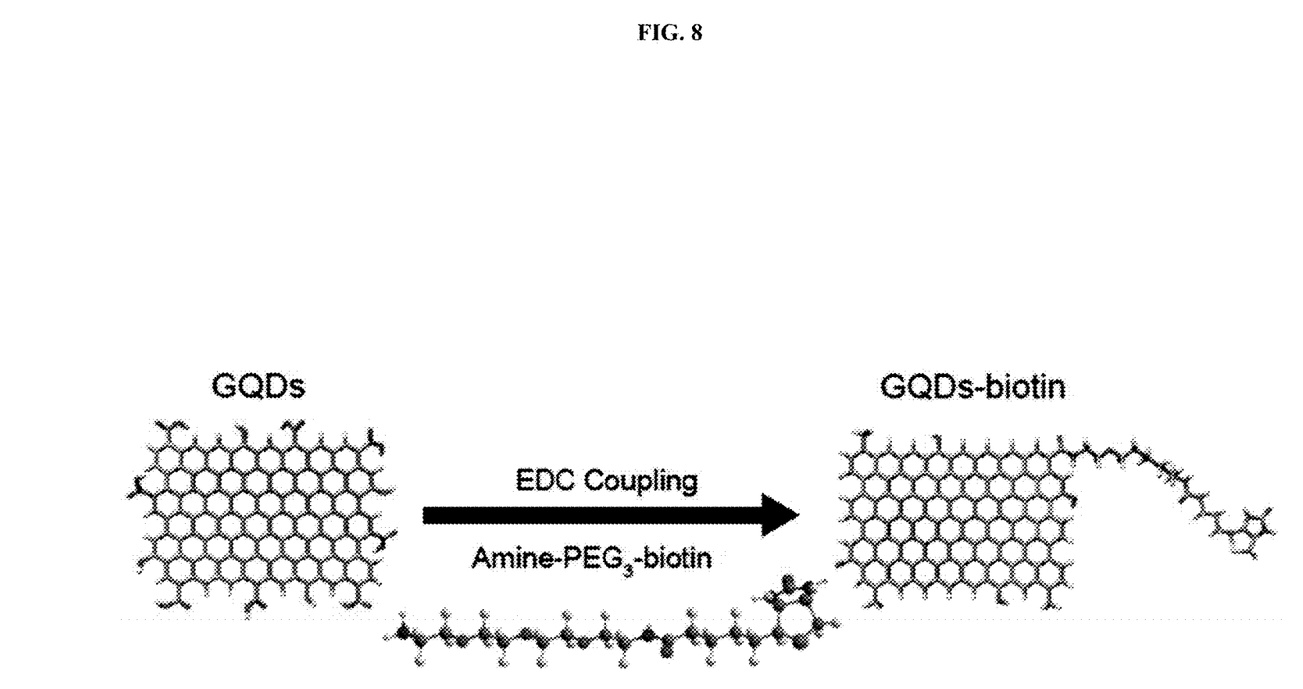
FIG. 8 is a reaction diagram of attaching biotin to graphene quantum dots.

Biotin was attached to GQDs to prepare traceable GQD-biotin (FIG. 8).

For whole tissue immunohistochemistry, paraffin of the paraffin slide was deparaffinized and then blocked with 5% normal goat serum-containing PBS. The sections were incubated with a biotin-primary antibody overnight and then incubated with an enzyme-linked secondary antibody followed by DAPI staining. Images were collected using a confocal microscope (Eclipse TE200, Nikon, Japan).

After GQD-biotin was injected into the abdomen of the rat, the cerebellum of the rat was treated with a biotin-antibody. As shown in FIG. 9, GQD (indicated by arrows in FIG. 9, CB: cerebellum, BS: brain stem) was detected in the cerebellum of rat injected with GQD-biotin.

EXPERIMENTAL EXAMPLE 6

Generation of GQDS and Distinction of Nano-GOs 6-1. Acquirement of Nano-GOs

Pristine graphene oxides (GOs) were synthesized via improved Hummer's method. In order to prepare nano-sized GOs, obtained GOs (3 mg/ml) in a distilled water solution were vigorously tip-sonicated for 3 hours, followed by vacuum-filtration using a cellulose nitrate membrane filter (0.45 μm, GE Healthcare).

6-2. Difference in Length Between GQDs and Nano-GOs Using TEM Photographs

A solution (10 μg/ml) dispersed a specimen prepared according to the manufacturing example was adsorbed on copper grids (Ted Pella, Inc.) coated with 300 mesh lacey carbon for 30 minutes. Prior to imaging, the grid was washed with a few drops of distilled water and thoroughly dried in a desiccator. The prepared specimen was analyzed with a high resolution-transmission electron microscope (HR-TEM, JEM-3010, JEOL Ltd.), and the images were collected with a Gatan digital camera (MSC-794) coupled to the microscope.

Figure 11:
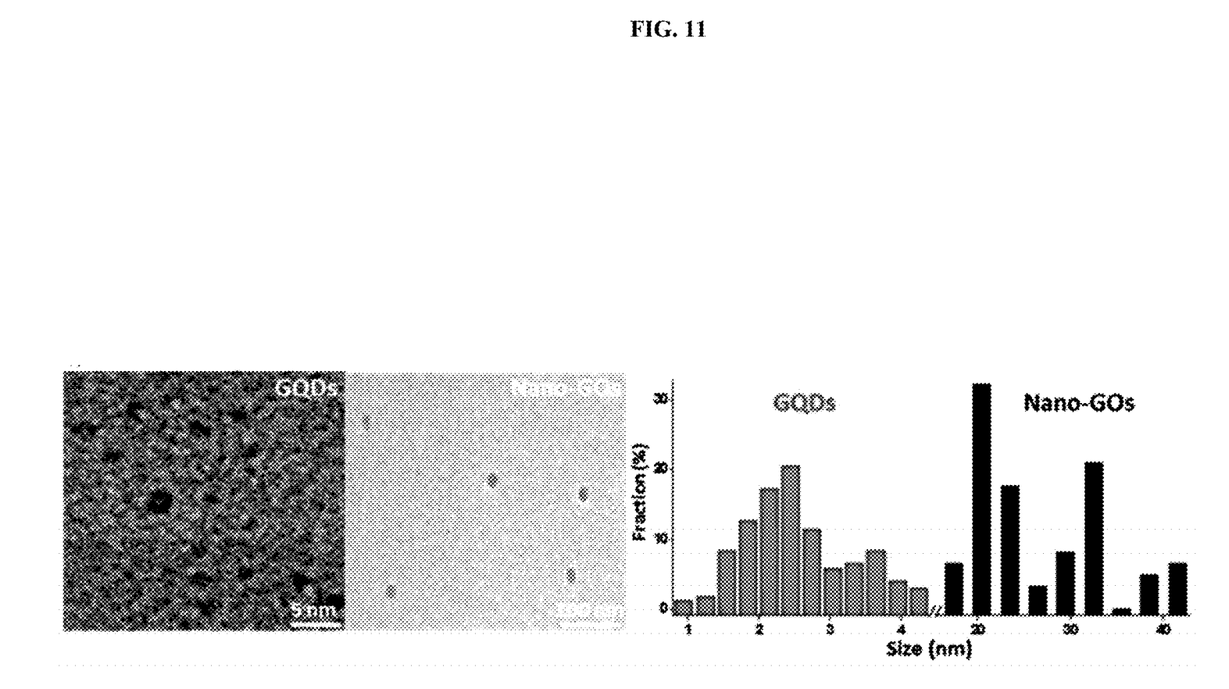
FIG. 11 is a comparison of sizes of graphene quantum dots and nano-graphene oxides.

As a result, using the TEM images, an average length of Nano-GOs was measured to be 28.5±9.7 nm, whereas that of GQDs was measured to be 2.8±1.0 nm (FIG. 11).

Figure 12:
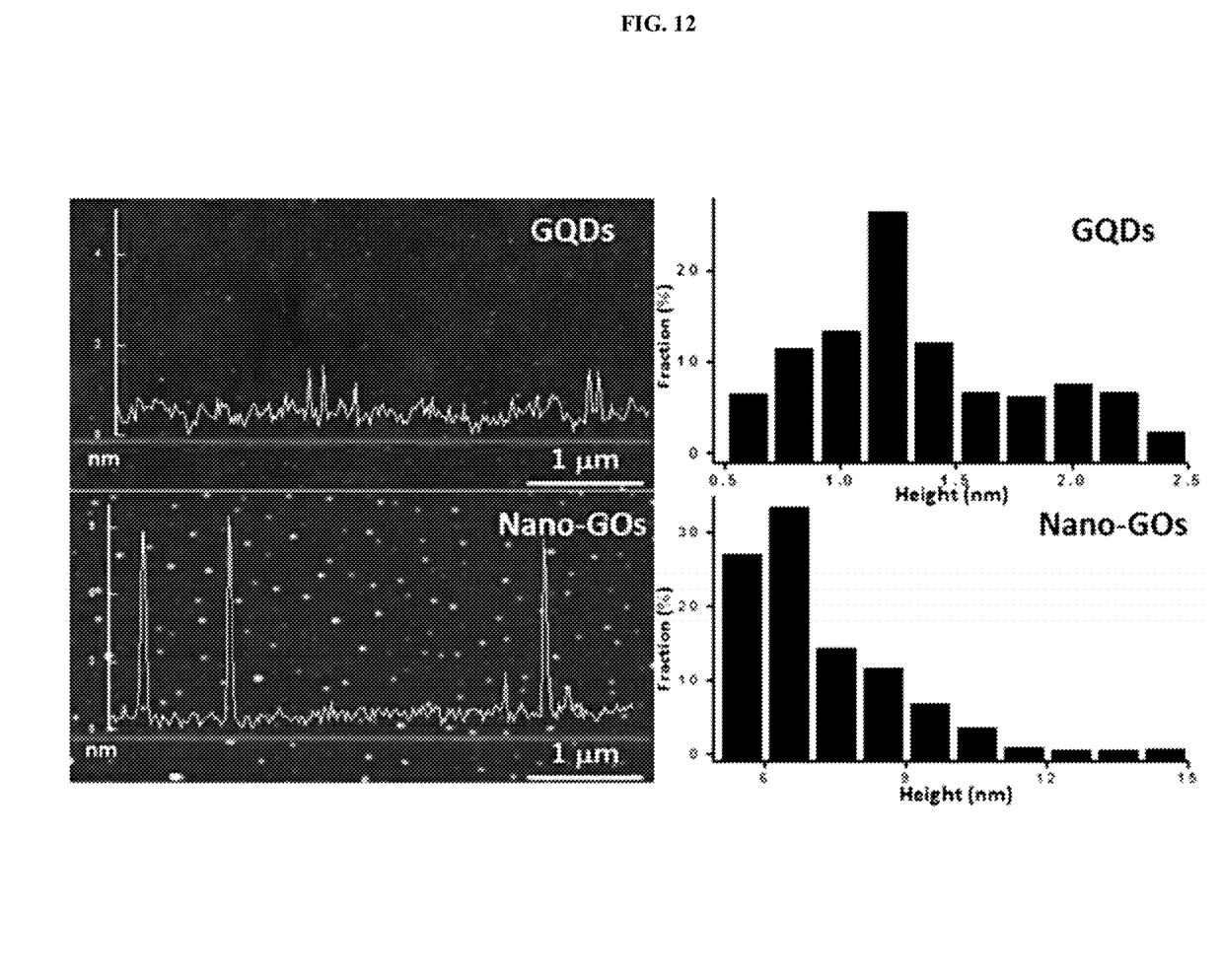
FIG. 12 is a comparison of sizes of graphene quantum dots and nano-graphene oxides.

6-3. Height Difference Between Two Substances Using Atomic Force Microscopy (AFM) Photographs When a height difference between the two substances was measured using AFM, an average height of Nano-GOs was measured to be 7.1±1.8 nm, whereas that of GQDs was measured to be 1.4±0.5 nm (FIG. 12).

6-4. Result of Raman Spectroscopy Measurement

Figure 13:
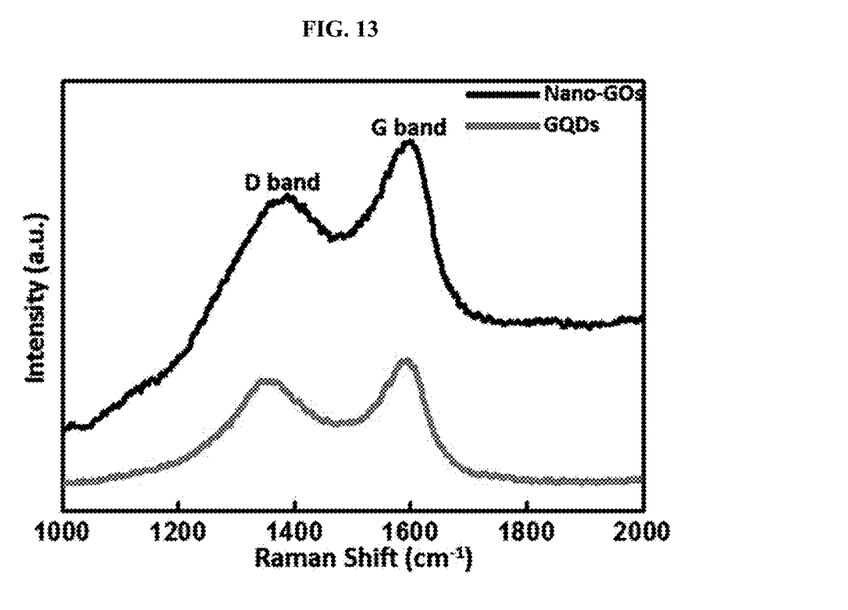
FIG. 13 is a result of Raman spectroscopy measurement of graphene quantum dots and nano-graphene oxides.

As a result of Raman spectroscopy measurement, the D and G bands (1360 and 1600 $cm^{-1}$) which are characteristic of graphene-based materials were measured for both Nano-GOs and GQDs. In the case of Nano-GOs, the D band is dense and wide because a defect site is included (FIG. 13).

Due to such differences, different results may be expected when Nano-GOs and GQDs are used in vivo.

The foregoing description of the present application is for illustrative purposes only, and those of ordinary skill in the art to which the present application pertains will be able to understand that other specific forms can be easily modified without changing the technical spirit or essential features of the present application. Therefore, it should be understood that the embodiments described above are illustrative and non-limiting in all respects. For example, each component described as a single type may be implemented in a distributed manner, and similarly, components described as being distributed may also be implemented in a combined form.

The scope of the present application is indicated by the claims to be described below rather than the detailed description, and all changes or modified forms derived from the meaning and scope of the claims, and their equivalent concepts should be interpreted as being included in the scope of the present application.

INDUSTRIAL APPLICABILITY

A pharmaceutical composition according to the present invention includes graphene quantum dots and is expected to be usefully utilized in preventing or treating lysosomal storage disorders by inhibiting accumulation of substrates in lysosomes or decomposing previously accumulated substrates by binding to unmetabolized substrates using a negative charge generated on a graphene quantum dot surface.

The invention claimed is:

1. A method for treating a lysosomal storage disorder, comprising administering to a subject having a lysosomal storage disorder a composition comprising graphene quantum dots as an active ingredient,
    wherein the graphene quantum dots have a length of 1 nm to 20 nm,
    wherein the graphene quantum dots comprise, as a terminal functional group, an oxygen atom-containing functional group selected from the group consisting of a carboxyl group, a ketone group, an aldehyde group, a hydroxy group, and an epoxy group, and
    wherein the lysosomal storage disorder is Niemann-Pick disease or Gaucher disease.

2. The method of claim 1, wherein the graphene quantum dots bind to unmetabolized cholesterol to inhibit accumulation of cholesterol in lysosomes or decompose previously accumulated substrates.

3. The method of claim 1, wherein the graphene quantum dots are nano-sized fragments of graphene oxide or reduced graphene oxide.

4. The method of claim 1, wherein the composition further comprises a pharmaceutically acceptable carrier or excipient.

* * * * *